(12) United States Patent
Shoelson

(10) Patent No.: US 6,993,959 B2
(45) Date of Patent: Feb. 7, 2006

(54) SYSTEM AND METHOD FOR THE ANALYSIS OF ATOMIC FORCE MICROSCOPY DATA

(75) Inventor: Brett Shoelson, Arlington, VA (US)

(73) Assignee: National Institutes of Health, Rockville, MD (US)

(*) Notice: Subject to any disclaimer, the term of this patent is extended or adjusted under 35 U.S.C. 154(b) by 0 days.

(21) Appl. No.: 10/686,738

(22) Filed: Oct. 17, 2003

(65) Prior Publication Data

US 2005/0081608 A1    Apr. 21, 2005

(51) Int. Cl.
*G01N 13/16* (2006.01)

(52) U.S. Cl. .............................. 73/105; 73/81; 702/189
(58) Field of Classification Search .................. 73/81, 73/105; 702/189
See application file for complete search history.

(56) References Cited

U.S. PATENT DOCUMENTS 5,193,383 A * 3/1993 Burnham et al. ............. 73/105
5,866,807 A * 2/1999 Elings et al. ................. 73/105
6,134,954 A * 10/2000 Suresh et al. .................. 73/81
6,883,367 B2 * 4/2005 Feng et al. ..................... 73/81

* cited by examiner

*Primary Examiner*—Daniel S. Larkin
(74) *Attorney, Agent, or Firm*—Venable, LLP; Jeffri A. Kaminski

(57) ABSTRACT

A system and method for the analysis of AFM data is provided. The system and method can be used in conjunction with an atomic force microscopy (AFM) system including a cantilever with a tip used to analyze a sample, the AFM outputting an AFM data file. An exemplary embodiment of the invention includes a computer readable medium storing computer readable program code for causing a computer to receive user input regarding an analysis to be performed and analysis parameters; parse the AFM data file based on the user input to obtain a deflection of the cantilever; determine an indentation depth of the tip into the sample based at least in part on the deflection; select a model of contact mechanics based on the user input; solve the selected model of contact mechanics based on the input analysis using the determined indentation depth; and determine a residual error.

25 Claims, 8 Drawing Sheets

SYSTEM AND METHOD FOR THE ANALYSIS OF ATOMIC FORCE MICROSCOPY DATA

BACKGROUND OF THE INVENTION

1. Field of the Invention

The present invention relates generally to a system and method for analyzing data and more particularly for analyzing data gathered by an atomic force microscope and determining characteristics of a sample.

2. Related Art

Atomic force microscopy (AFM) is rapidly emerging as an important tool in microrheology and nanotechnology. The ability of AFM to create three dimensional micrographs with resolution down to the nanometer and angstrom scales has made it an essential tool for imaging surfaces in applications ranging from semiconductor processing to cell biology. The AFM can also probe nanomechanical and other fundamental properties of sample surfaces including their elastic and adhesive properties.

An example of a typical AFM is shown in FIG. 1. The AFM 10 includes a cantilever 12 having a tip of a known shape 14 that is used to sense a force between the sample 16 and the tip 14. As the tip 14 is moved along the surface of or perpendicular to the sample, the tip 14 deflects depending upon the force exerted on the tip 14. An electromagnetic beam 18, such as a laser beam, is directed at a reflective surface on the end of the cantilever 12. The beam 18 is reflected from the cantilever. The reflected beam 20 is detected by a photodetector 22, such as a split photodiode. Movement of the tip can be correlated to the movement of the reflected beam 20 on the photodetector 22. The size and position of the current created in the photodetector 22 are linked via detector electronics 24 to a control computer 26. A feedback loop between the detector electronics 24 and the control computer 26 is provided to maintain the cantilever position at a defined location on the surface that is being analyzed. The control computer 26 controls the movement of the microscope along the X, Y and Z-axes. Fine motion piezoelectric controllers are used to generate the precise motion that is needed to generate topographic images and force measurements. A piezoelectric controller is a device that moves by a precise amount when a voltage is applied across its electrodes. The piezoelectric controllers are used to control and place the tip 14 along the surface of the sample 16. The nanoscale deflections of the tip and the feedback voltages required to maintain this deflection can provide many different types of data regarding the sample. For example, reliable data relating normal forces to indentation depths of the sample can be calculated. This data can be used to determine the modulus of elasticity for the sample. In one specific example, the modulus of elasticity can be detected for small tissue samples or even on individual cells. This affords new and potentially invaluable information regarding tissue and cell properties and can lead to improvements in predictive and heuristic models of the behavior of biomaterials.

The force sensed by the AFM is calculated by multiplying the deflection of the cantilever by the cantilever's spring constant. This force is then typically plotted versus cantilever position as a force curve. The force curve provides a graphic way of seeing how much force is exerted on a cantilever probe at a given cantilever position. However, the quantitative analysis of the cantilever position and tip deflection data is extremely difficult and time-consuming. Few people approach the problem in the same way. Additionally, there is considerable debate concerning the best method of dealing with nonlinearities inherent in AFM, which portion of the force curve to analyze, or whether the data should be evaluated at constant force or at constant indentation. These problems are compounded by the uncertainty in determining an initial point of contact of the tip with the sample. Thus, a great deal of subjectivity is introduced into standard AFM analyses.

The use of idealized models of contact mechanics to describe real data may require solving an assortment of technical problems. Foremost among these in this application is the difficulty of determining the exact point at which the tip contacts the sample. Known contact forces including attractive electrostatic charges and repulsive coulombic forces can induce tip motion and complicate the assessment of tip contact. Additionally, certain models used in determining the force and elasticity of the sample require certain assumptions, which are not always appropriate.

Thus, there is a need for a method and system which can minimize errors in interpreting AFM data. The system and method should allow for a systematic diminution of the potential error in AFM analyses. The system should be automated and be able to process large amounts of data accurately in a short period of time.

BRIEF SUMMARY OF THE INVENTION

In an exemplary embodiment of the invention, a system and method for the analysis of AFM data is provided. The system and method can be used in conjunction with an atomic force microscopy (AFM) system including a cantilever with a tip used to analyze a sample, the AFM outputting an AFM data file. An exemplary embodiment of the invention includes a computer readable medium storing computer readable program code for causing a computer to receive user input regarding an analysis to be performed and analysis parameters; parse the AFM data file based on the user input to obtain a deflection of the cantilever; determine an indentation depth of the tip into the sample based at least in part on the deflection; select a model of contact mechanics based on the user input; solve the selected model of contact mechanics based on the input analysis using the determined indentation depth; and determine a residual error.

According to another embodiment of the invention a computer readable medium storing computer readable program code for causing a computer to present an option Graphical User Interface (GUI) to a user; receive test parameters from the user via the GUI; read an AFM data file based on the input test parameters; plot a graph of the deflection of the cantilever versus a position of the cantilever in a GUI; present in a GUI a first user actuated interface for initiating an analysis; and perform an elasticity analysis of the data file based on the input parameters in response to actuation of the first user actuated interface.

In another embodiment of the invention, a system for analyzing data is provided. The system comprises an atomic force microscopy (AFM) system including a cantilever with a tip used to analyze a sample, the AFM outputting an AFM data file. A memory stores the AFM data file and is in communication with the AFM. A computer reads the AFM data file from the memory. A display is coupled to the computer for displaying output from the computer. Input means are coupled to the computer to receive user input. Means for parsing the AFM data file based on the user input to obtain a deflection of the cantilever. The system also includes means for determining an indentation depth of the tip into the sample based at least in part on the deflection; means for selecting a model of contact mechanics based on the user input; and means for solving the selected model of contact mechanics using the determined indentation depth to obtain a result.

Further objectives and advantages, as well as the structure and function of preferred embodiments will become apparent from a consideration of the description, drawings, and examples below.

BRIEF DESCRIPTION OF THE DRAWINGS

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention.

Embodiments of the present invention provide a system and method for the analysis of AFM data. An exemplary embodiment of the invention is described below in the analysis of the elasticity of a material. However, the system and method can also be applied in different types of analyses. The method can be performed via a software program, such as a computer readable medium storing program instructions to cause a computer to carry out the various processes.

Figure 1:
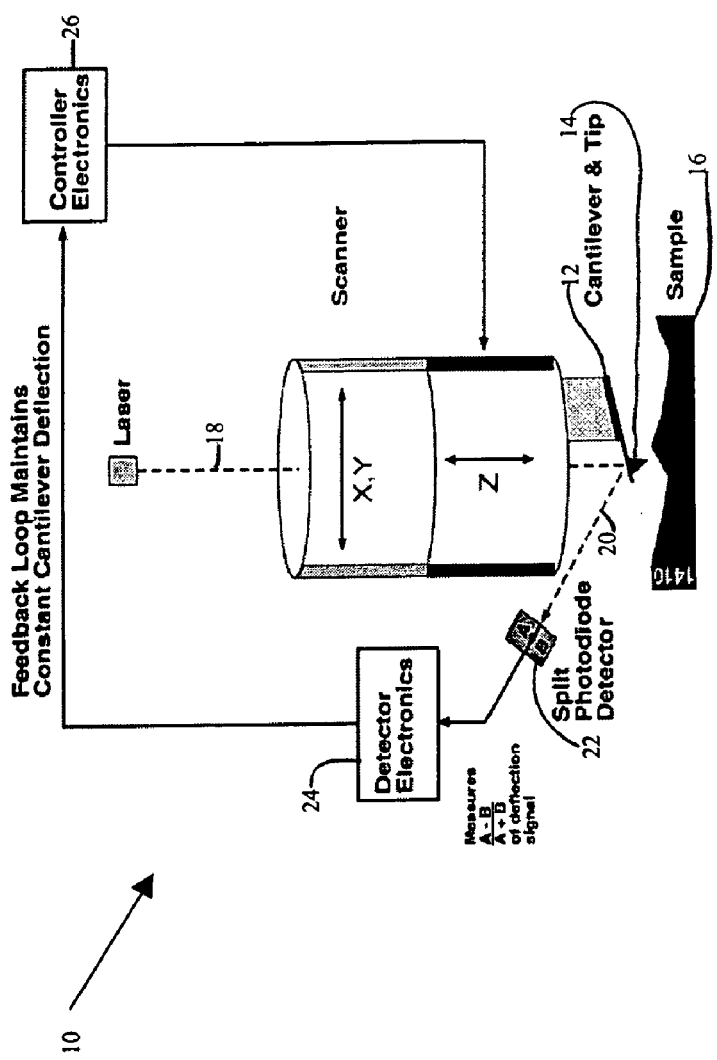
FIG. 1 depicts an exemplary embodiment of a known AFM.

An AFM such as that shown in FIG. 1 can be used to gather data used in an elasticity analysis. The AFM is operated in an indentation mode. In the indentation mode, a head of the microscope 10 is moved towards and away from the sample in a direction substantially perpendicular to the surface of the sample being measured. The piezoelectric controllers position the AFM at a precise location along the X and Y-axes. The X and Y-axes define the plane of the surface of the sample. Once the AFM is in the desired position, the piezoelectric controllers then move the cantilever 12 along the Z-axis towards the surface of the sample 16. As the tip 14 on the cantilever 12 is moved toward the surface of the sample 16, the cantilever 12 deflects in response to various forces on it. As the cantilever 12 engages the sample, the tip 14 of the cantilever 12 may begin to penetrate the surface of the sample 16, to a degree that depends on the hardness of the sample. This penetration causes an indentation in the sample. The cantilever continues to moves towards the sample until a selected distance is reached. The cantilever then begins to move away from the sample. As the cantilever moves, the deflection of the cantilever tip and the cantilever position are measured. The AFM is then moved to another position in the X, Y plane and the process is repeated. The measured data can then be used to determine the depth of the indentation and the elasticity of the sample.

For example, assume that the surface of the sample is very hard. In that case, the tip does not penetrate into the sample. Once the tip comes into contact with the surface of the material, for every unit the cantilever moves down, the cantilever tip deflects one unit up. However, in a softer sample, the tip indents the surface of the sample and is not deflected upward a distance equal to the downward movement of the cantilever. The difference in the deflection of the cantilever in these two cases can be used to determine the depth of the indentation in the soft sample. This information can be used to determine the elasticity of the sample.

A series of measurements is made as the cantilever moves along the Z axis with the AFM held at the same point on the X and Y axes. The measurements include the deflection of the cantilever tip and the force applied to the cantilever as the cantilever is moved downward towards the sample surface and away from the sample surface. These data are then stored in a file, such as a computer readable file stored in a database or other computer readable memory. The data file may include a header which identifies the file and the parameters of the measurement, such as information regarding the AFM, the cantilever, voltage range, etc. Following the header is the payload. The payload includes the measurements of the deflection of the cantilever tip and the force applied to the cantilever. The payload is typically a list of numbers. The exact format of the data file depends on the AFM and software version used to create it and may vary. This data can be used to generate a force curve for the measured point on the sample.

Figure 2:
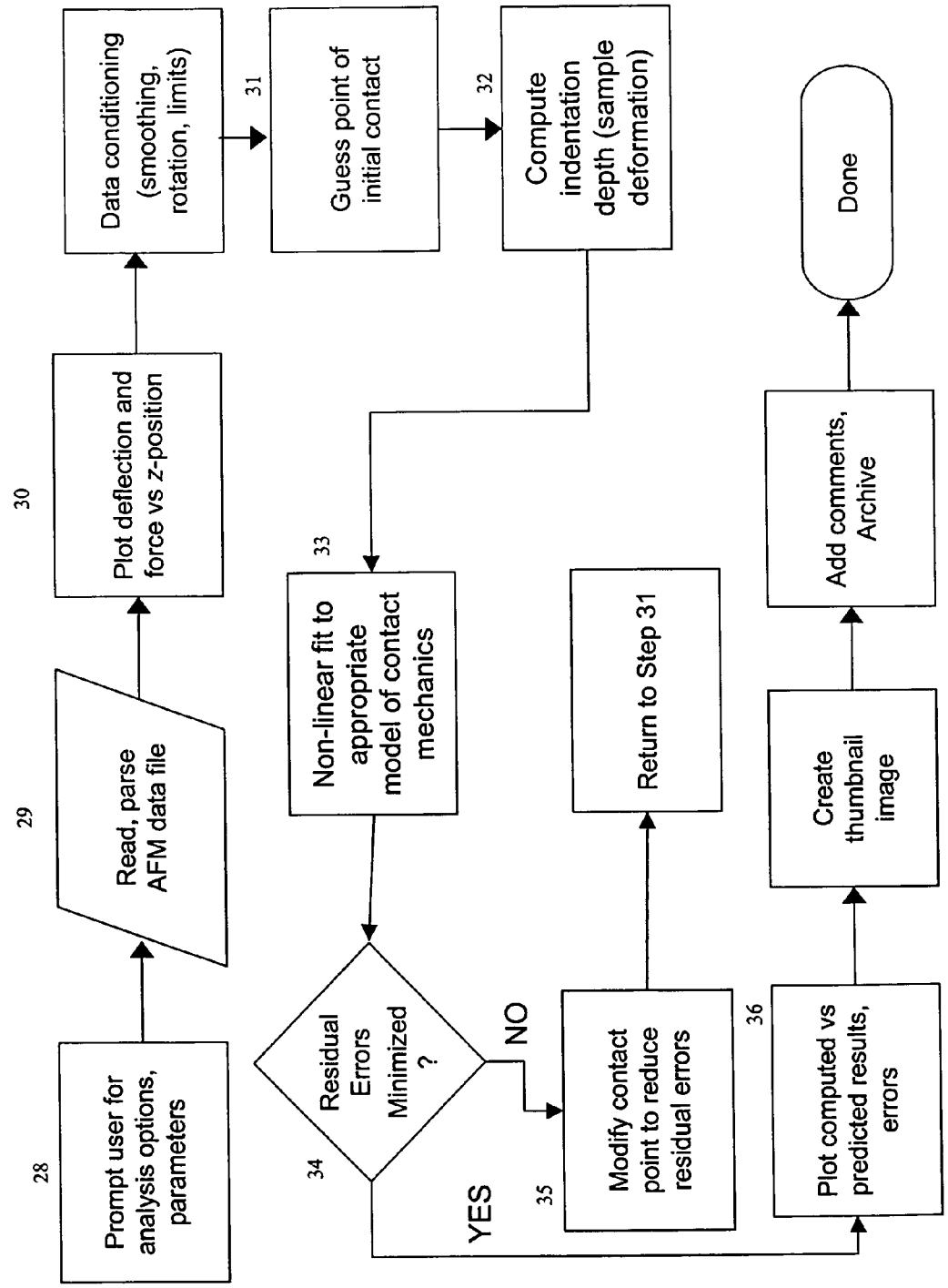
FIG. 2 is a flow chart depicting a process according to an exemplary embodiment of the present invention.

Once the data are gathered, the task of analyzing the data and extracting useful information begins. In an exemplary embodiment of the invention, a software program for analyzing the AFM data is provided. A flow chart illustrating a process for analyzing the data is shown in FIG. 2. The software provides a graphical user interface (GUI) intensive computational tool that automates the reconstruction, analysis, and interpretation of AFM data.

Figure 3:
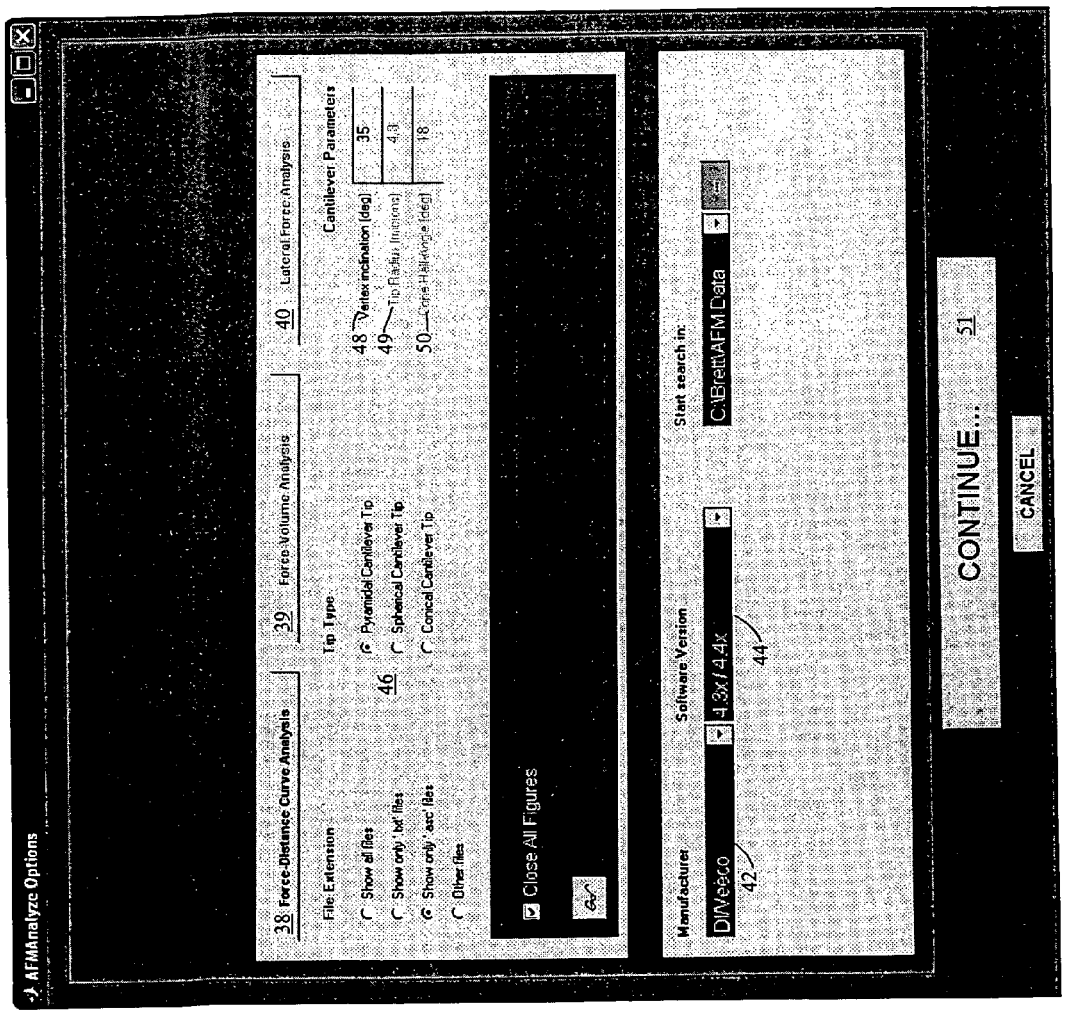
FIG. 3 is a Graphical User Interface according to an exemplary embodiment of the present invention.

An example of a GUI that can be displayed to a user of the software package is shown in FIG. 3. The GUI 37 is one of the initial screens presented to the user. This interface prompts the user for information about the AFM parameters and the analysis to be performed, per step 28. Buttons 38–40 allow the user to select the type of analysis to be performed. In the example shown, the user can select from a force-distance curve analysis, a force-volume analysis, and a lateral force analysis. Additionally, various menus can also be provided to allow the user to input information regarding the parameters of the test. For example, the GUI 37 can include fields 42, 44 to allow the user to select from the different types of AFMs used to gather the data and the software used to store the data in the file. Fields 42, 44 may include drop down menus that allow the user to select from the various supported AFMs and software. The user can also input the type of tip used for the test via menu 46. Depending on the type of tip selected, different input fields 48–50 are activated. For example, in FIG. 3 the user has selected a pyramidal tip. Accordingly, the field 48 for inputting a vertex inclination of the tip is activated. Additional fields may be provided to enter the spring constant of the cantilever as well as the vertex inclination, tip radius, cone angle, etc. The user clicks button 51 when they are finished entering information.

Once the user has completed inputting information, the AFM data file is read, based at least in part on the analysis selected by the user and the other parameters input by the user, per step 29. The AFM data file is automatically parsed to locate the data that are relevant to the requested analysis. Based on the type of AFM used to collect the data and the type of software used to create the data file, it can be determined where in the data file the relevant information is stored. For example, a data file created using a DI/Veeco AFM with version 4.3 software creates a data file having a particular format. The user has previously input this information via GUI 37. With the knowledge of the type of data file, the format of the file can be determined and the relevant information can be easily located. The data file is then read to extract this information.

Figure 4:
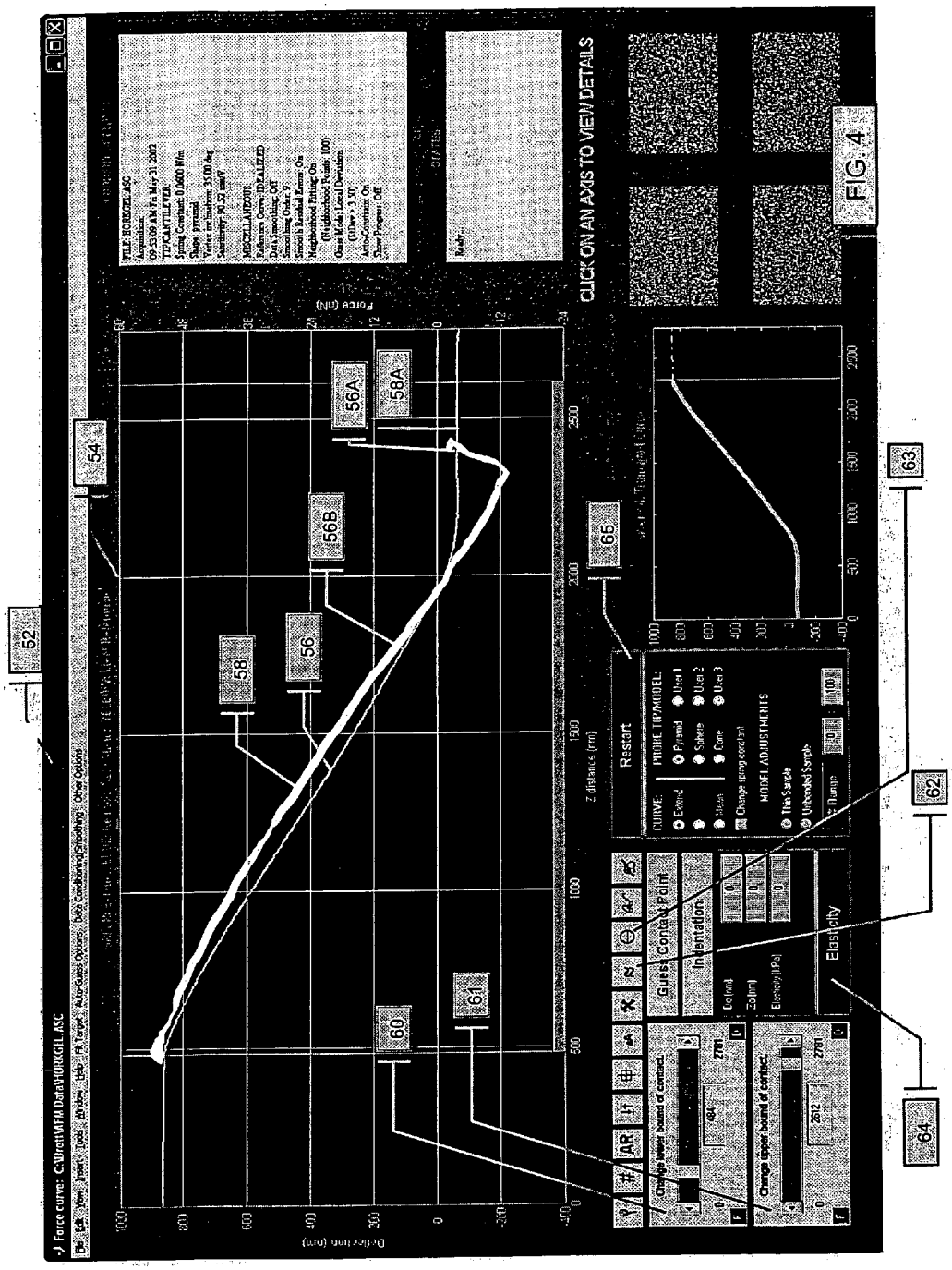
FIG. 4 is a Graphical User Interface according to an exemplary embodiment of the present invention.
Figure 5:
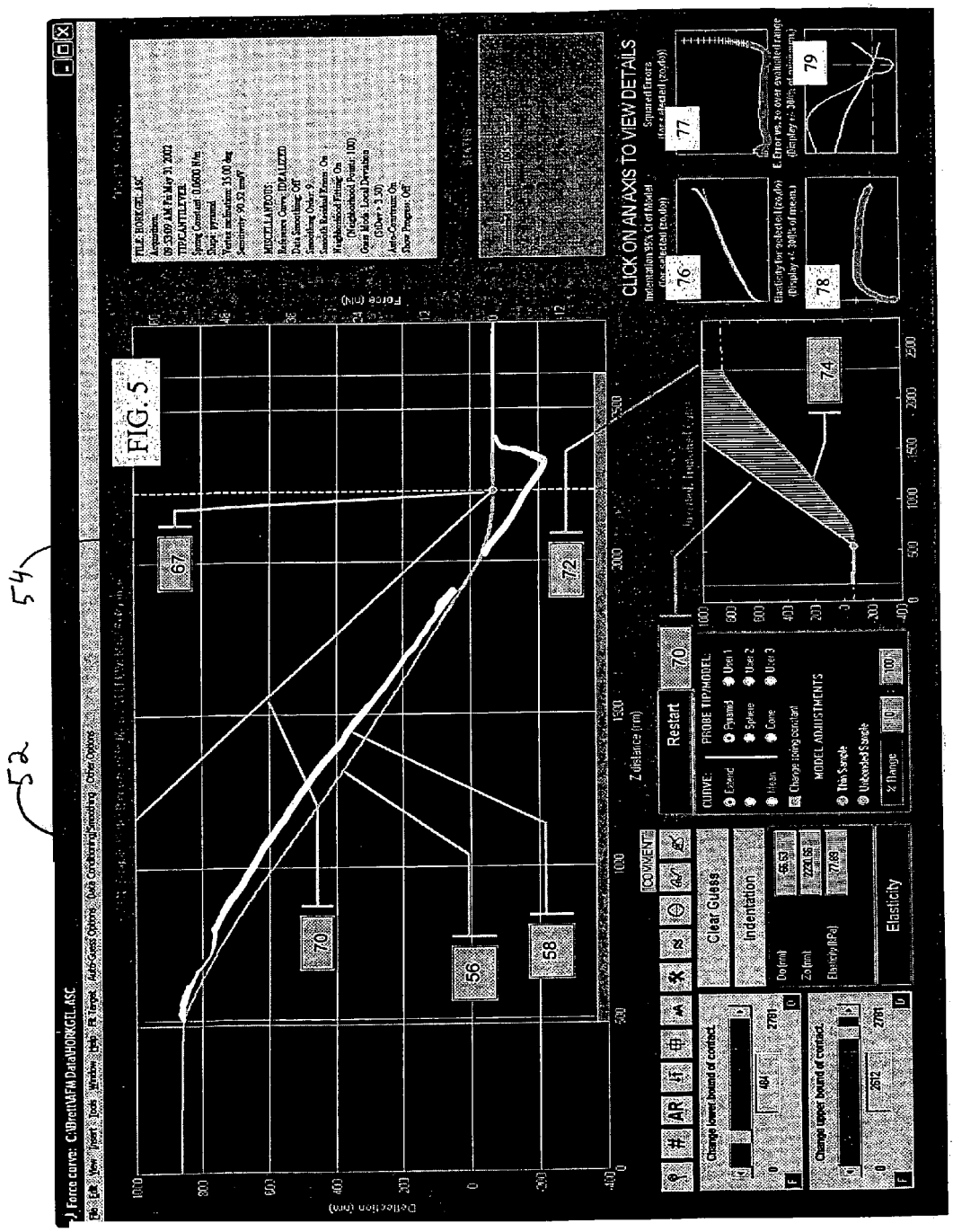
FIG. 5 is a Graphical User Interface according to an exemplary embodiment of the present invention.

Once the data are read from the file, the deflection of the tip and force versus the Z position of the cantilever can be determined, plotted and displayed to the user per step 30. An exemplary GUI 52 for this purpose is shown in FIGS. 4 and 5. Force can be calculated based on the deflection of the cantilever and the stiffness of the cantilever using Hooke's law, $F=-kZ$, where F is the force, k is the stiffness of the cantilever, and Z is the distance the cantilever is deflected. An example of a force curve is shown in window 54 of GUI 52. The force curve includes two partially overlapping curves, an extend curve 56 and a retract curve 58. The extend curve 56 represents the measurements taken as the cantilever tip moves towards the sample. As can be seen in FIG. 4, initially there is no deflection of the cantilever tip as the tip has yet to contact the surface of the sample. This is represented as the flat portion 56A of curve 56. As the tip approaches the surface of the sample, the cantilever begins to deflect and the curve 56 begins to move towards the upper left of the figure, represented by inclined portion 56B. Note that as the tip approaches the sample, the distance Z decreases and the curve 56 moves from right to left.

The retract curve 58 represents the measurements as the cantilever tip moves away from the sample. As the cantilever tip is withdrawn from the sample, the force exerted on the cantilever and the deflection of the cantilever decreases, while the distance Z increases. In the example shown, the force exerted on the cantilever continues to decrease until the tip is disengaged from the surface of the sample and the retract curve 58 correspondingly flattens out at portion 58A, as shown in FIG. 4. In an ideal representation, the extend curve 56 and retract curve 58 would largely overlap. However, due to the nonlinearities inherent in the AFM piezoelectronics, characteristics of the sample and environmental conditions, the extend curve 56 and retract curve 58 may be offset, as shown in FIG. 4.

GUI 52 also provides an interface for the user to access additional functionality. For example, the user can use GUI 52 to change an area of the curves being analyzed. Slide bars 60, 61 can be used to vary the upper and lower bounds of the data to be analyzed. Also, buttons or other selection features can be provided to allow the user to access other data processing functions. Actuating button 62 provides access to several data-smoothing algorithms, which can also include user definable parameters. Actuating button 63 provides curve rotation options for the correction of overall slant of the data set. Data smoothing may entail using polynomial curve-fitting algorithms with a user-specified number of terms, or application of another smoothing routine such as a box or Gaussian filter, with a user-specified fitting order. Data rotation may entail prompting the user to select two distinct points on a portion of the curve that should be horizontal, calculating the deviation from horizontal, and rotating the entire curve by the calculated angle. Actuating button 63 initiates the creation of new GUI controls for selection of the horizontal points.

The data represented in curves 56, 58 can be used to determine the elasticity of the sample. Depressing elasticity button 64 in GUI 52 can start the process. One of the initial steps in the elasticity analysis is to estimate the point at which the tip initially contacts the sample, the initial contact point (step 31). The analysis is then based on that estimated initial contact point. In the past, this estimation was done visually by a user making a guess of the point on the curves 56, 58 where the contact point should be. This is typically in the vicinity of the curve where it begins to incline. Obviously, the visual method can lead to errors and differences between analyses of the same data performed by different users. Moreover, an error in selecting the contact point results in an error that is propagated throughout the elasticity analysis. Thus, embodiments of the present invention automatically select a contact point and then modify the selection by minimizing the residual error associated with it.

One process for estimating the initial contact point is discussed below. As mentioned above, data points are read from the AFM data file in step 28. Once the data points are read, the mean of a subset of points is calculated from the non-contact end of the data. The subset is continually expanded to include the next data point in the series. As the subset is expanded, the extent to which each newly included point deviates from the previous subset is calculated. The first point at which ten consecutive, newly included data values differ from the previous subset by a user-specified number of standard deviations is selected as an initial estimate of the contact point. In addition to receiving user input to define the number of standard deviations, user input may define the number of consecutive data points that must differ by the speficied standard deviation. Of course, other selection criteria may be used without departing from the scope of the invention. The user can select the data set to be evaluated via GUI 52. Window 65 in GUI 52 provides a menu via which the user can select from available data sets. The data sets include the data points making up the extend curve 56, that is the Z position versus the deflection of the cantilever as the microscope head of the AFM is moved towards the sample, the data points making up the retract curve 58, or a mean of the two curves 56, 58. The estimated initial contact point 67 is then displayed in window 54 of GUI 52 (FIG. 5).

Once the initial contact point is estimated, the depth of the indentation of the cantilever tip into the sample is determined in step 32. In the described embodiment, this is done by comparing a force curve for the measured sample with the force curve of an ideal sample. Alternatively, it may be done by comparing a force curve to data curves representing real, hard materials. The ideal sample is a theoretical hard material into which the tip of the cantilever does not penetrate. Thus in the ideal sample case the cantilever deflects linearly with the position of the microscope head as the head is moved along the Z-axis. An example of a force curve for an ideal sample, called here an ideal curve, is shown in FIG. 5. The ideal curve 70 has a slope of one and extends linearly from the current estimate of the initial contact point 67. The difference between the measured cantilever deflection represented in curves 56, 58 and that represented by the ideal curve 70 is the amount of indentation of the tip 14 into the sample 16. Window 72 in GUI 52 provides a visual representation of the calculation of the indentation depth. The amount of deflection at any point along the Z-axis is determined by the difference between the ideal curve 70 and the user selected measured curve 74, which is one of the extend curve 56, retract curve 58 or the mean of the two. The vertical lines between curves 70 and 74 represent the calculated indentation depth. Thus, the indentation depth of the tip can be determined at a plurality of points as the cantilever is moved along the Z-axis.

The calculated indentation depth is then used to determine the elasticity of the sample. This can be done by calculating Young's modulus based on the calculated indentation depths. The indentation depths are fit using nonlinear algorithms to any one of several models of classical contact mechanics per step 33. Exactly which model of contact mechanics is selected depends on the user-selected shape of the contact probe. For instance, for a spherical tip, the sample indentations are fit to a Hertzian model. This also allows the user to correct for thin or unbonded samples. For a pyramidal tip, the indentation depths are fit to a Bilodeau model and for a conical tip the sample indentation depths are fit to a Sneddon model. The equations for the Hertz, Bilodeau, and Sneddon models, respectively, are reproduced below:

$$\delta_{uncorrected} = [3F(1-v^2)/4E\sqrt{R}]^{2/3}$$

$$\delta_{4-sided} = [(\pi/2)F(1-v^2)/E \tan \alpha]^{1/2}$$

$$\delta = [2.0126F(1-v)\tan \alpha/E]^{1/2}$$

where F=force, v=Poisson's ratio for the sample, E=Young's modulus, R=tip radius, and α=tip angle.

The above equations are solved for E which gives the Young's modulus for the sample. In step 34, residual errors are then determined. The residual error represents the deviation of the actual data from what the data would be in the selected model of contact mechanics. For example, if a Sneddon model is selected, the equation for the Sneddon model produces a curve comprised of data points representing indentation depth. The actual indentation depth calculated in step 32 may or may not lie on the Sneddon curve. The difference between the actual indentation depth and the model is the residual error. The error can be calculated using a number of known methods, for example, the sum of squares method. The error for each of the data points is combined together to obtain the total residual error.

The amount of residual error depends largely on the estimated initial contact point. An analysis performed at other contact points may produce a better result. Therefore a process for reducing or minimizing the residual error is performed in step 35. In an exemplary embodiment, the steps 31–35 are repeated using new values for the initial contact point until the residual errors are minimized or reduced. The new values of the initial contact point are constrained to the curve of interest, that is the curve 56, 58 or mean thereof used in the calculating the indentation depth in step 33. In the described example, the initial contact point is changed simply by sliding it along the curve of interest. For example, fifty data points to the left of the initially estimated contact point 67 and fifty data points to the right of the initially estimated contact point can be used as subsequent guesses for the initial contact point. These points need not be consecutive nor uniformly spaced. For calculation efficiency, adaptive step sizing may be used, with the spacing of guesses decreasing in the neighborhood of error minima. The process continues to step 32 and a new indentation depth is computed using an ideal curve extending from the new initial contact point. For each guess of the initial contact point, indentation depths are recomputed and new nonlinear fits are performed per step 33. The residual errors for the newly calculated indentation depths are then compared with each other. The contact point that provides the lowest residual error is selected. Then, the computed versus predicted errors and results using the selected contact point can be plotted and displayed to a user. Additionally, the results may be archived as shown in the flow chart of FIG. 2

Figure 6:
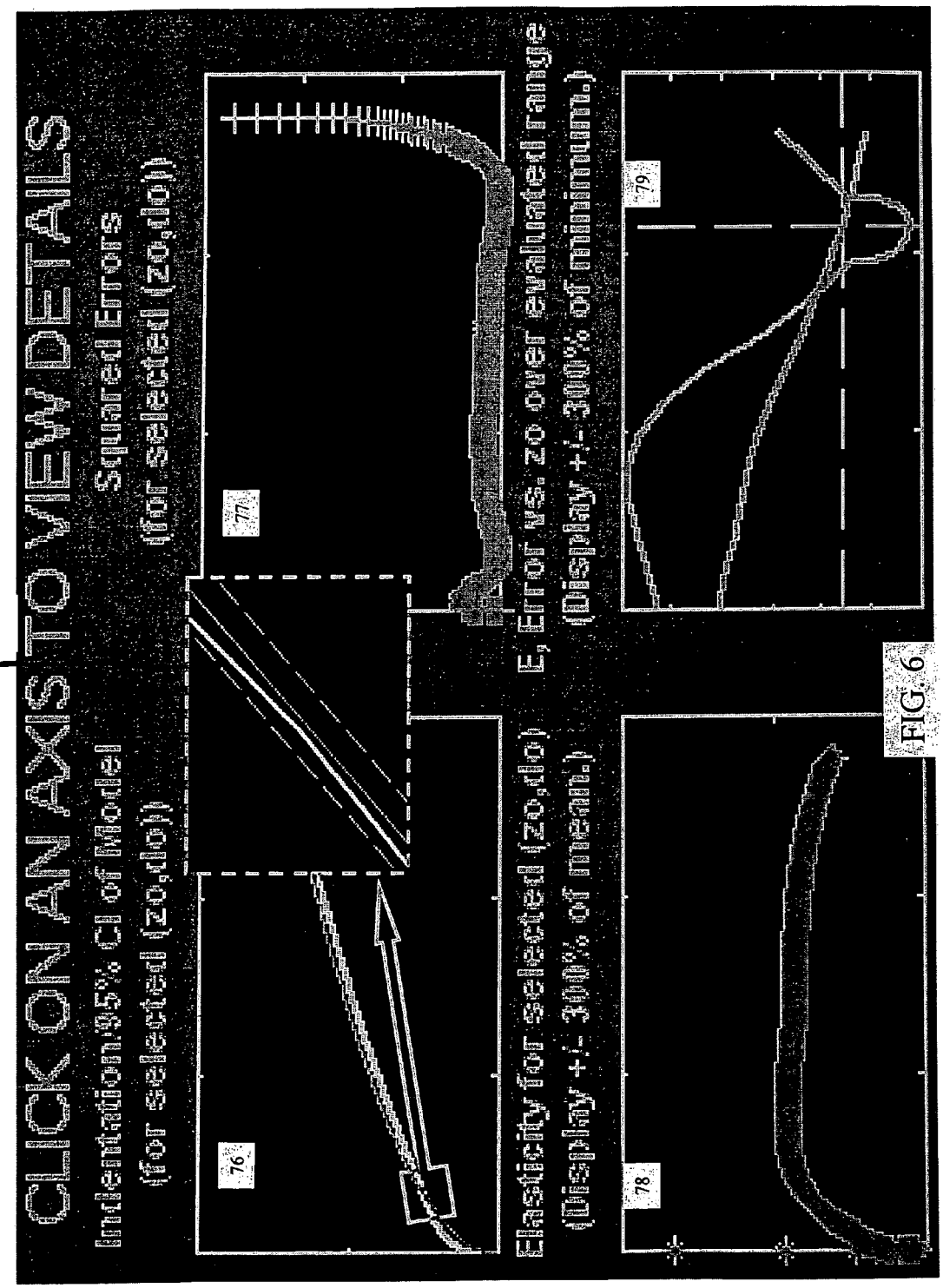
FIG. 6 is an expanded view of FIG. 5.

In FIG. 5, GUI 52 includes four windows displaying graphs 76–79 representing the results of the analysis. FIG. 6 is a blown up view of these graphs. Graph 76 illustrates the indentation depth versus the 95% confidence interval for the theoretical (modeled) curve. The inset 76A shows a portion of the indentation curve in relation to the theoretical curve and 95% confidence interval of the theoretical curve. Graph 77 illustrates the point-by-point error of the actual force curve versus the theoretical force curve for the contact point having minimized-error. Graph 78 illustrates the "best-fit" value of the elasticity modulus of the sample for the contact point having minimized-error. Horizontal data in graph 78 suggests a stable fit. Deviations from horizontal may prompt analyses of different subsets of data, or modifications of the analysis parameters. Graph 79 is a plot of elasticity modulus overlaying the sum-of-squared error for all points evaluated as candidate contact points. Final calculations are based on the point corresponding to the minimized error (vertical dashed line). The discontinuity in the slope of the error curve reflects the use of adaptive step-sizes, whereby data are sampled more finely in the region of the minimum. This optimizes accuracy and speed of calculation.

Figure 7:
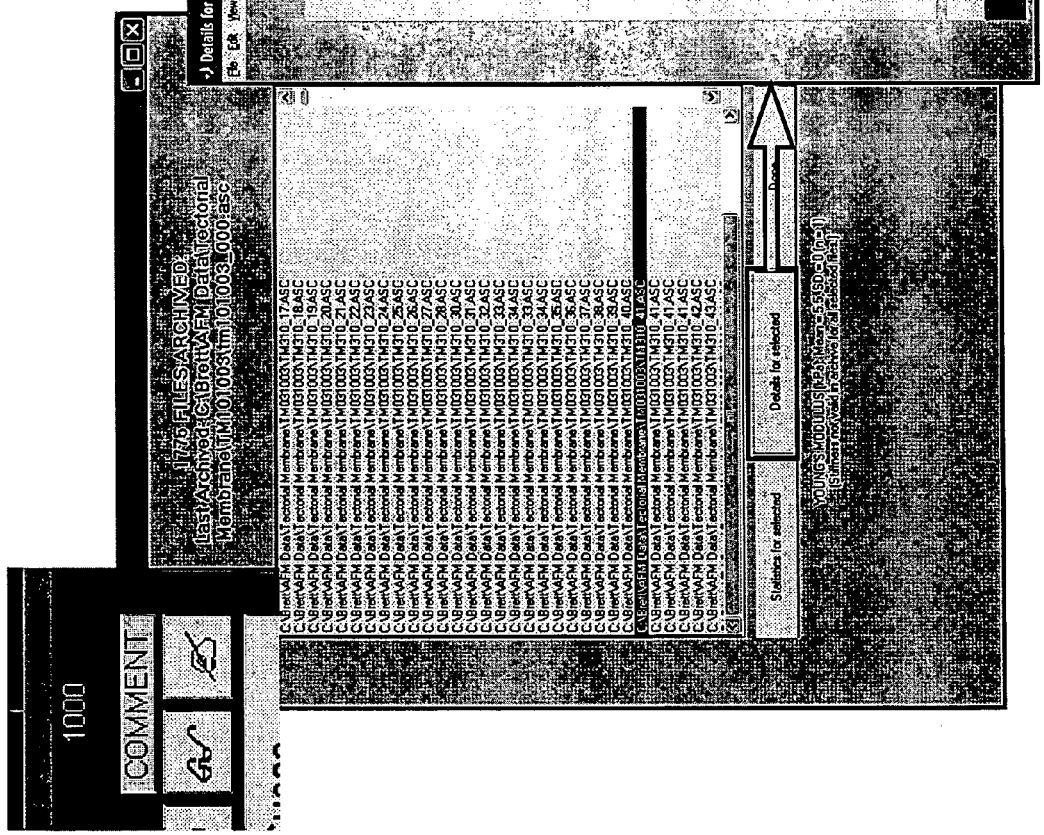
FIG. 7 illustrates an interactive link to an output text file according to an exemplary embodiment of the invention.

The results of the analysis can also be displayed, manipulated and stored in numerical and textual form. GUI 52 provides buttons or other means for accessing this functionality. The results of the analysis can be stored to a text file as shown in FIG. 7. The result can be displayed to the user within the GUI environment. The user may examine the descriptive statistics of a group of data, the details of a single analysis or other information. The user may also reconstruct the analysis using previously stored parameters.

Figure 8:
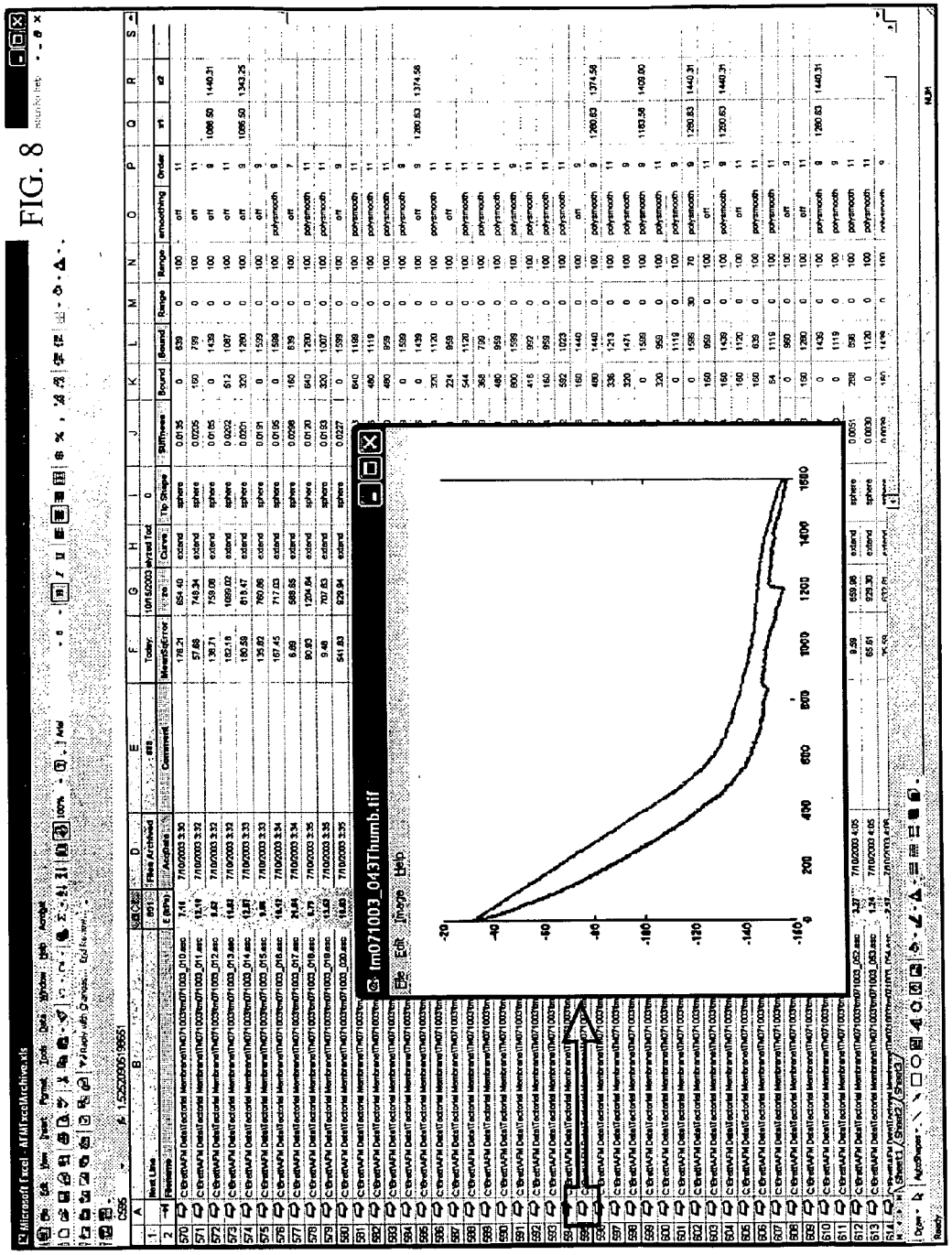
FIG. 8 illustrates an output spreadsheet file according to an exemplary embodiment of the invention

Additionally, the results of the analysis can be stored in spreadsheet form. For example, FIG. 8 shows the results output to an Excel spreadsheet. The results are automatically linked to the spreadsheet. Each set of results is stored along with a thumbnail sketch of the data curves for subsequent retrieval and evaluation, as shown in the flowchart of FIG. 2. Each of the results of the analysis along with the parameters of the analysis can be stored. Each parameter and result can be assigned to its own field in the spreadsheet. In the example shown, the tip shape, curve analyzed, stiffness, etc. are each displayed in a field of the spreadsheet. This allows the data to be both easily viewed and manipulated.

Although a process for determining the elasticity of a sample is discussed above, the model of contact mechanics can be solved for any value. For example, the process can be used for calibration of the cantilever using materials with known properties. In this case the Young's modulus is know. The appropriate equation for the contact mechanics is then solved for the tip parameters.

Accordingly, embodiments of the invention provide a computational tool that automates the reconstruction, analysis, and interpretation of AFM data. At the press of a button a user can determine the elasticity of a measured sample. The tedious and time consuming task of manual and algorithmic analysis is eliminated and large numbers of data sets can be analyzed quickly.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. For example, the claims refer to a second GUI for purposes of clarity. The second GUI may be the same as, different from or a partially redrawn antecedent GUI.

What is claimed is:

1. In an atomic force microscopy (AFM) system including a cantilever with a tip used to analyze a sample, the AFM outputting an AFM data file, a computer readable medium storing computer readable program code for causing a computer to perform the steps of:
    a) receiving user input regarding an analysis to be performed and analysis parameters;
    b) parsing the AFM data file based on the user input to obtain a deflection of the cantilever;
    c) determining an indentation depth of the tip into the sample based at least in part on the deflection;
    d) selecting a model of contact mechanics based on the user input;
    e) solving the selected model of contact mechanics based on the input analysis using the determined indentation depth; and
    f) determining and reducing a residual error.

2. A computer readable medium of claim 1, further comprising computer readable program code for causing a computer to perform the step of displaying results of the analysis to a user.

3. A computer readable medium of claim 1, wherein the analysis parameters comprise at least one of a tip shape, a spring constant, a tip radius, a vertex inclination, and a cone angle.

4. A computer readable medium of claim 1, wherein the determining the indentation depth comprises:
    estimating an initial contact point;
    determining data points of an ideal curve that extends from the estimated initial contact point; and
    determining a difference between the data points comprising the ideal curve and the deflection of the cantilever.

5. A computer readable medium of claim 4, wherein the estimating step comprises:
    reading data points from the AFM data file in a serial manner;
    continuously calculating a mean of the data points as the data points are read;
    continuously calculating a standard deviation for the data points as the data points are read; and
    finding a first occurrence of a predetermined number of data points that exceed or are exceeded by the current mean by a predetermined number of standard deviations.

6. A computer readable medium of claim 5, further comprising computer readable program code for causing a computer to perform the step of receiving the predetermined number of data points and the predetermined number of standard deviations as user input.

7. A computer readable medium of claim 1, further comprising fitting the indentation depths using a nonlinear algorithm to the selected model of contact mechanics.

8. A computer readable medium of claim 1, wherein the selected model of contact mechanics is one of a Hertz, Bilodeau, and Sneddon model.

9. A computer readable medium of claim 1, wherein determining the residual error comprises determining a difference between the measured indentation depths and indentation depths resulting from the solved model of contact mechanics.

10. A computer readable medium of claim 1, further comprising computer readable program code for causing a computer to perform the step of reducing the residual error.

11. A computer readable medium of claim 10, wherein reducing the residual error comprises:
    selecting at least one new initial contact point;
    repeating c)–f) using the new initial contact point; and
    comparing the residual errors; and
    selecting the initial contact point with the lowest residual error.

12. A computer readable medium of claim 1, further comprising computer readable program code for causing a computer to perform the steps of:
    presenting a first Graphical User Interface (GUI) to a user;
    receiving the analysis parameters from the user via the GUI;
    reading the AFM data file based on the input analysis parameters;
    plotting a graph of the deflection of or force on the cantilever versus a position of the cantilever in a second GUI;
    presenting in the second GUI a first user actuated interface for initiating an analysis; and
    performing an elasticity analysis of the data file based on the input analysis parameters in response to actuation of the first user actuated interface.

13. A computer readable medium of claim 12, further comprising computer readable program code for causing a computer to perform the steps of:
    presenting in the second GUI a second user actuated interface for modifying a region of interest function;
    presenting in the second GUI a third user actuated interface for data smoothing function;
    presenting in the second GUI a fourth user actuated interface for a curve rotation function.

14. A computer readable medium of claim 13, further comprising computer readable program code for causing a computer to perform the steps of:
    modifying the region of interest in response to actuation of the second user actuated interface;
    performing the data smoothing function interest in response to actuation of the third user actuated interface; and
    performing the curve rotation function interest in response to actuation of the fourth user actuated interface.

15. A computer readable medium of claim 12, further comprising computer readable program code for causing a computer to perform the step of displaying at least one of a confidence interval graph, a squared error graph, an elasticity graph, and an elasticity/error graph.

16. A computer readable medium of claim 12, further comprising computer readable program code for causing a computer to perform the step of formatting results of the analysis into a text file.

17. A computer readable medium of claim 16, further comprising computer readable program code for causing a computer to perform the step of displaying the text file to the user.

18. A computer readable medium of claim 12, further comprising computer readable program code for causing a computer to perform the step of formatting the results of the analysis into a spreadsheet format.

19. A computer readable medium of claim 18, further comprising computer readable program code for causing a computer to perform the step of associating each parameter and the results of the analysis with a predetermined field.

20. A computer readable medium of claim 18, further comprising computer readable program code for causing a computer to perform the steps of:
creating a thumbnail view of a data curve for the analysis; and
storing the thumbnail view with the results.

21. A system for gathering and analyzing data, comprising:
an atomic force microscopy (AFM) system including a cantilever with a tip used to analyze a sample, the AFM outputting an AFM data file;
a memory for storing the AFM data file and in communication with the AFM;
a computer to read the AFM data file from the memory;
a display coupled to the computer for displaying output from the computer;
input means coupled to the computer to receive user input;
means for parsing the AFM data file based on the user input to obtain a deflection of the cantilever;
means for determining an indentation depth of the tip into the sample based at least in part on the deflection;
means for selecting a model of contact mechanics based on the user input; and
means for solving the selected model of contact mechanics using the determined indentation depth to obtain a result.

22. The system of claim 21, further comprising means for reducing a residual error in the result.

23. The system of claim 21, further comprising means for formatting results of the analysis into a text file.

24. The system of claim 21, further comprising means for formatting the results of the analysis into a spreadsheet format.

25. The system of claim 21, further comprising:
means for plotting a graph of the deflection of the cantilever versus a position of the cantilever in a Graphical User Interface (GUI); and
means for presenting in the GUI a user actuated interface for initiating an analysis.

* * * * *